Nov. 7, 1950 E. PRUSHEK Plant Pat. 987
CHRYSANTHEMUM PLANT
Filed Nov. 28, 1949
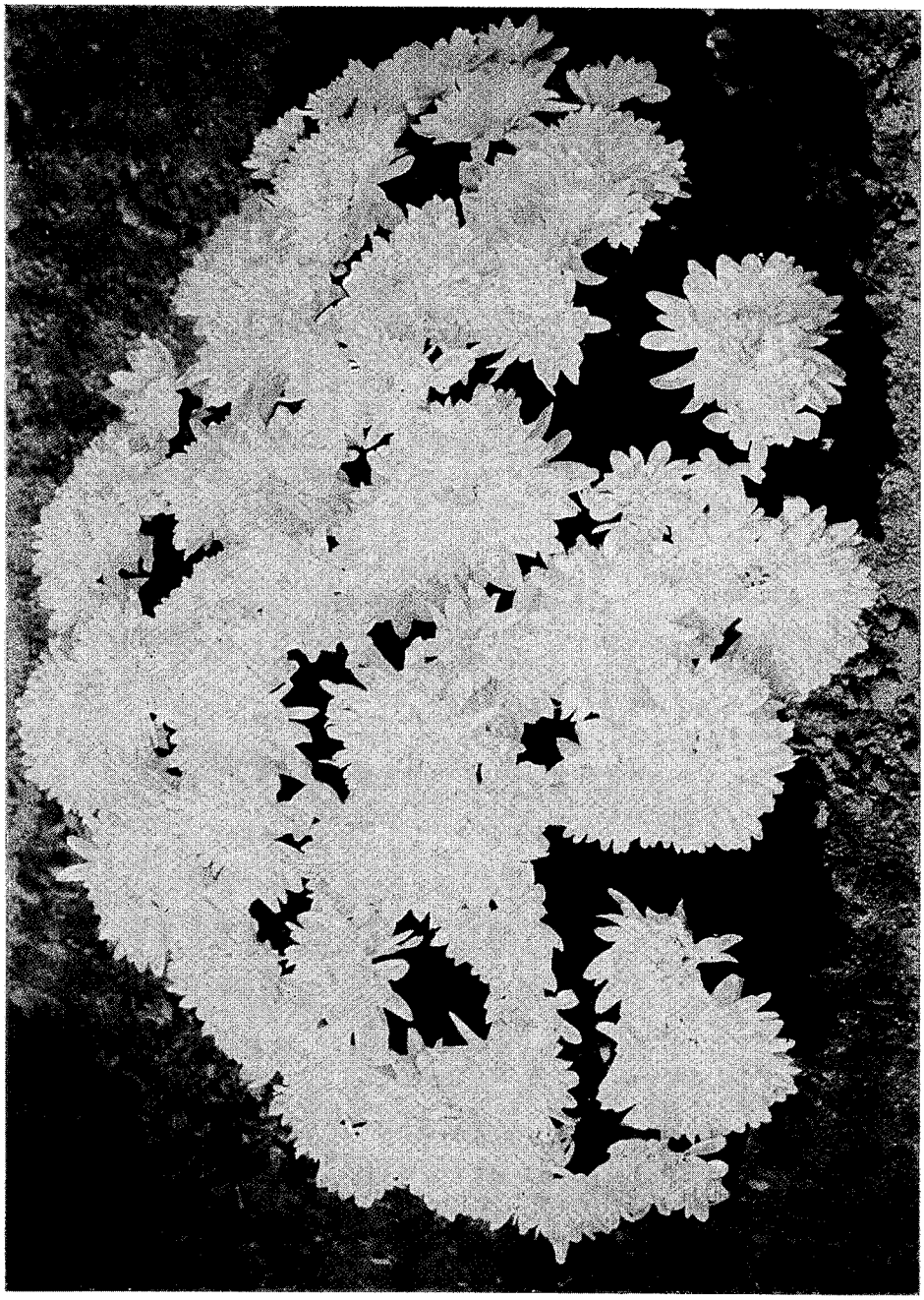
Inventor:
Emil Prushek
By Robb & Robb,
Attorneys Patented Nov. 7, 1950

Plant Pat. 987

UNITED STATES PATENT OFFICE

987

CHRYSANTHEMUM PLANT

Emil Prushek, Niles, Mich., assignor to The R. M. Kellogg Company, Three Rivers, Mich., a corporation of Michigan Application November 28, 1949, Serial No. 129,715

1 Claim. (Cl. 47—60)

My present invention comprises a new and distinct variety of chrysanthemum plant, the result of crossing two unnamed, white flowered, chrysanthemum seedlings.

The object of my invention, in general, was to produce a new variety of chrysanthemum of the cushion type but of much more dwarf and compact plant form than the older varieties of cushion chrysanthemums, and especially to produce such a very dwarf and compact variety of chrysanthemum having blooms of a desirable white color and having certain desirable characteristics in reference to early flowering, longer season, and longer and more consistent color life of its blooms.

The development of the present new variety has resulted from a program which I have been conducting of careful selection and cross-breeding with the view of producing new varieties of chrysanthemum of much more dwarf and compact habits of growth in different desired colors in reference to the blooms of such plants.

The result of the specific hybridization above mentioned has been to produce my present new and distinct variety of chrysanthemum characterized by its very dwarf and compact habits of growth, its early flowering, its long season due to the long and consistent color life of the individual blooms, the large size of the blooms, the massing of the blooms to cover the foliage, and the white color of the blooms.

My new variety is so different from either of its parents that there is little basis for comparison and my new variety is also quite unlike any other present variety. The color of the blooms of my new variety is most distinctive in that the color is a nearly pure white from the time of opening of the flower until the usual petal browning of old age. By way of contrast, the standard "White Cushion" variety has blooms whose color is a shade of pink as the blooms open, the color fading to white and then again turning pink with age so that the blooms have a white color for a short time only.

My new variety blooms about three weeks earlier than the variety "White Cushion" and although my new variety because of its earlier blooming season is more exposed to the sun, heat and rain, the color of the blooms remains consistent throughout the blooming period.

In regard to the early blooming habit of my new variety, it may be mentioned that the average time of opening of the blooms is around September 25, and the average date of full bloom is about October 1, in the region of Niles, Michigan, in reference to first year plants from soft top cuttings.

The average length of the blooming season of my new variety extends from about September 25 to October 20.

The flowers of my new variety are unusually large for a plant so small and the large size of the blooms is therefore a quite distinctive characteristic of my new variety. The flowers of my new variety average two and one-half (2½) inches in diameter as compared with an average diameter of two inches for the blooms of the variety "White Cushion."

In reference to the distinctive dwarf and compact habit of growth of my new variety, it may be mentioned that first year plants from soft top cutting average sixteen inches in diameter and nine inches in height, in reference to plants grown in fields in the region of Niles, Michigan. On the other hand, plants of the variety "White Cushion" grown under the same conditions in the same region average twenty-four inches in diameter and sixteen inches in height.

Because of the large size of the bloom of my new variety, it may be compared with the variety "Glacier," the blooms of which average about three inches in diameter. However, the bush height in reference to habits of growth, as represented by "Glacier" and my new variety are entirely different. "Glacier" is upright, more open and the blooms are sparser. On the other hand, my new variety is compact, squatty and the blooms mass together to almost completely hide the foliage, giving the appearance of a mass of white when in bloom. The flowers of my new variety have fuller centers and better substance for longer life when compared to the blooms of "Glacier."

The flowers of my new variety open at about the time of the opening of the earliest blooming chrysanthemum varieties and the substance and consistency of color continue effective over a relatively long period.

My new variety has been found to retain its distinctive characteristics through successive asexual reproduction.

A typical plant of my new variety of chrysanthemum is shown in the accompanying drawing forming a part hereof.

The following is a detailed description of my new variety of chrysanthemum plant, the color references being to the Horticultural Chart of the British Colour Council:

Classification: Botanic—*Chrysanthemum hortorum.*

*Flower*

Blooming habit: Blooms early; profusely. Recurrent—continuous, late summer and fall.

Bud:

*Size.*—Small.

*Form.*—Globular.

Is not affected by wet weather.

Is not affected by hot weather.

*Color.*—When sepals first divide—Mimosa Yellow 602/3. When petals begin to unfurl—white. When half blown—inside of petal—reverse of petal—pure white with light Dresden Yellow 64/3 blush at base of petals.

*Sepals.*—Smooth edge. Stand up.

*Opening.*— Bud opens well and is not affected by hot or wet weather.

Bloom:

*Size.*—Medium.

*Average size when fully expanded.*—2½''.

*Borne.*—In clusters.

*Stems.*—Medium, normal.

*Form.*—When first open—flat. Permanence—retains its form to the end.

*Petalage.*—Very double.

*Number of petals.*—Under normal conditions, about 150.

*Color*—Center of flower—Dresden Yellow 64/3. Outer petals—pure white. Base of petals—Dresden Yellow 64/2. Inside of petals—white; reverse of petals—white. General tonality from a distance—white, gleaming. General color tonality at the end of—first week—white, with a touch of yellow at center; second week—white; center faded to white; third week—white, with some browning of older petals.

Petals:

*Texture.*—Thin, soft. Not affected by hot or wet weather; though an early blooming white variety, it stands sun, heat and rain.

*Appearance.*—Satiny inside, satiny outside.

*Form.*—Oval, notched.

*Arrangement.*—Imbricated.

*Fragrance.*—Characteristic chrysanthemum.

*Lastingness.*—Very long.

Genital organs:

*Color.*—Yellow.

*Arrangement.*—Regular.

*Stamens, filaments (threads).* — Short. Color—lemon yellow.

*Pollen.*—Gold yellow.

*Styles.*—Medium, thin.

*Stigmas.*—Yellow.

*Plant*

Form: Bush.

Growth: Medium, dwarf, compact.

Foliage:

*Size.*—Small.

*Quantity.*—Normal.

*Color.*—New foliage—upper side: normal green; under side: light green. Old foliage—upper side: normal green; under side: light green.

*Shape.*—Oval pointed, serrated.

*Texture.*—Velvety on upper side; rough on under side.

*Edge.*—Serrated.

*Serration.*—Double, large sharp.

*Leaf stem.*—Green; under side—rough.

*Stipules.*—Medium, smooth.

*Disease resistance.*—Resistant to leaf spot.

Wood:

*New wood.*—Color—light green. Bark—rough.

*Old wood.*—Color—green. Bark—rough.

I claim:

A new and distinct variety of chrysanthemum plant substantially as herein disclosed, characterized as to novelty by its dwarf, compact growth, its early flowering, its long blooming season, the long and consistent color life of its blooms, the large size of the blooms, the massing of the blooms to cover the foliage, and the white color of the blooms.

EMIL PRUSHEK.

No references cited.